United States Patent
Leach et al.

(10) Patent No.: US 7,179,391 B2
(45) Date of Patent: Feb. 20, 2007

(54) APPARATUS AND METHOD FOR SEPARATING AND CONCENTRATING FLUIDS CONTAINING MULTIPLE COMPONENTS

(75) Inventors: Michael Leach, Warsaw, IN (US); Jennifer E. Woodell-May, Leesburg, IN (US); Joel Higgins, Claypool, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 378 days.

(21) Appl. No.: 10/445,381

(22) Filed: May 23, 2003

(65) Prior Publication Data

US 2004/0251217 A1  Dec. 16, 2004

Related U.S. Application Data

(60) Provisional application No. 60/383,013, filed on May 24, 2002.

(51) Int. Cl.
*B01D 17/038* (2006.01)
*B01D 21/26* (2006.01)
*B04B 1/02* (2006.01)

(52) U.S. Cl. ............... 210/782; 210/781; 210/789; 210/380.1; 604/6.01; 604/218; 604/403; 494/37; 494/43; 494/50; 422/72; 422/101

(58) Field of Classification Search ........... 210/781, 210/782, 787, 789, 360.1, 380.1, 516, 37; 422/72, 101; 494/43, 50; 604/6.01, 6.05, 604/218, 403
See application file for complete search history.

(56) References Cited

U.S. PATENT DOCUMENTS 280,820 A   7/1883  Hickson (Continued)

FOREIGN PATENT DOCUMENTS

EP   0 142 339   11/1984

(Continued)

OTHER PUBLICATIONS

Harvest Technologies Brochure, SmartPReP 2, (2002).

(Continued)

*Primary Examiner*—David A Reifsnyder
(74) *Attorney, Agent, or Firm*—Harness, Dickey & Pierce, P.L.C.

(57) ABSTRACT

An apparatus that allows for separating and collecting a concentrated fraction of a fluid, such as a whole blood sample, adipose tissue, or a bone marrow sample. The apparatus, when used with a centrifuge, allows for the creation of at least three fractions in the apparatus. It also provides for a new method of extracting the buffy coat phase from a whole blood sample. The apparatus includes a container to be placed to a centrifuge after being filled with a whole blood sample. A buoy or fraction separator, which has a density less than that of red blood cells of a whole blood sample, is disposed in the container. During the centrifuge process the buoy separates the red blood cells from another fraction of the whole blood. After the centrifuge process is finished a plunger is used to produce at least two other fractions, including a plasma fraction and a buffy coat. Then, the buffy coat may be removed from the container without commingling the fractions of the sample.

60 Claims, 5 Drawing Sheets

U.S. PATENT DOCUMENTS

| | | |
|---|---|---|
| 593,333 A | 11/1897 | Park |
| 3,409,165 A | 11/1968 | Creith |
| 3,508,653 A | 4/1970 | Coleman |
| 3,814,248 A | 6/1974 | Lawhead |
| 3,850,369 A | 11/1974 | Bull et al. |
| 3,879,295 A | 4/1975 | Glover et al. |
| 3,897,343 A | 7/1975 | Ayers |
| 3,909,419 A | 9/1975 | Ayers |
| 3,931,018 A | 1/1976 | North, Jr. |
| 3,957,654 A | 5/1976 | Ayres |
| 3,982,691 A | 9/1976 | Schlutz |
| 4,001,122 A | 1/1977 | Griffin |
| 4,046,699 A | 9/1977 | Zine, Jr. |
| 4,055,501 A | 10/1977 | Cornell |
| 4,077,396 A | 3/1978 | Wardlaw et al. |
| 4,152,270 A | 5/1979 | Cornell |
| 4,187,979 A | 2/1980 | Cullis et al. |
| 4,269,718 A | 5/1981 | Persidsky |
| 4,322,298 A | 3/1982 | Persidsky |
| 4,416,654 A | 11/1983 | Schoendorfer et al. |
| 4,417,981 A | 11/1983 | Nugent |
| 4,464,167 A | 8/1984 | Schoendorfer et al. |
| 4,511,662 A | 4/1985 | Baran et al. |
| 4,617,009 A | 10/1986 | Ohlin et al. |
| 4,675,117 A | 6/1987 | Neumann et al. |
| 4,776,964 A | 10/1988 | Schoendorfer et al. |
| 4,818,386 A | 4/1989 | Burns |
| 4,850,952 A | 7/1989 | Figdor et al. |
| 4,917,801 A | 4/1990 | Luderere et al. |
| 4,929,242 A | 5/1990 | Desecki et al. |
| 4,939,081 A | 7/1990 | Figdor et al. |
| 4,957,637 A | 9/1990 | Cornell |
| 5,019,243 A | 5/1991 | McEwen et al. |
| 5,047,004 A | 9/1991 | Wells |
| 5,053,134 A | 10/1991 | Luderer et al. |
| 5,131,907 A | 7/1992 | Williams et al. |
| 5,141,645 A | 8/1992 | Shiraki et al. |
| 5,147,290 A | 9/1992 | Jonsson |
| 5,165,938 A | 11/1992 | Knighton |
| 5,171,456 A | 12/1992 | Hwang et al. |
| 5,178,602 A | 1/1993 | Wells |
| 5,185,001 A | 2/1993 | Galanakis |
| 5,203,825 A | 4/1993 | Haynes et al. |
| 5,234,608 A | 8/1993 | Duff |
| 5,269,927 A | 12/1993 | Fiehler |
| 5,271,852 A | 12/1993 | Luoma, II |
| 5,318,782 A | 6/1994 | Weis-Fogh |
| 5,322,620 A | 6/1994 | Brown et al. |
| 5,344,752 A | 9/1994 | Murphy |
| 5,370,802 A | 12/1994 | Brown |
| 5,387,187 A | 2/1995 | Fell et al. |
| 5,393,674 A | 2/1995 | Levine |
| 5,403,272 A | 4/1995 | Deniega et al. |
| 5,456,885 A | 10/1995 | Coleman et al. |
| 5,474,687 A | 12/1995 | Van Vlasselaer |
| 5,494,578 A | 2/1996 | Brown et al. |
| 5,494,592 A | 2/1996 | Latham, Jr. et al. |
| 5,560,830 A | 10/1996 | Coleman et al. |
| 5,577,513 A * | 11/1996 | Van Vlasselaer ............ 600/578 |
| 5,585,007 A | 12/1996 | Antanavich et al. |
| 5,601,727 A | 2/1997 | Bormann et al. |
| 5,607,579 A | 3/1997 | Latham, Jr. et al. |
| 5,614,106 A | 3/1997 | Payrat et al. |
| 5,632,905 A | 5/1997 | Haynes |
| 5,646,004 A | 7/1997 | Van Vlasselaer |
| 5,648,223 A | 7/1997 | Van Vlasselaer |
| 5,663,051 A | 9/1997 | Vlasselaer |
| 5,674,173 A | 10/1997 | Hlavinka et al. |
| 5,707,331 A | 1/1998 | Wells et al. |
| 5,707,876 A | 1/1998 | Levine |
| 5,736,033 A | 4/1998 | Coleman et al. |
| 5,840,502 A | 11/1998 | Van Vlasselaer |
| 5,895,346 A | 4/1999 | Wells et al. |
| 5,916,743 A | 6/1999 | Lake et al. |
| 5,938,621 A | 8/1999 | Kelly et al. |
| 5,955,032 A | 9/1999 | Kelly et al. |
| 5,958,253 A | 9/1999 | Holm |
| 6,022,306 A | 2/2000 | Dumont et al. |
| 6,025,201 A | 2/2000 | Zelmanovic et al. |
| 6,051,146 A | 4/2000 | Green et al. |
| 6,053,856 A | 4/2000 | Hlavinka |
| 6,054,122 A | 4/2000 | MacPhee et al. |
| 6,063,297 A | 5/2000 | Antanavich et al. |
| 6,071,423 A | 6/2000 | Brown et al. |
| 6,090,793 A | 7/2000 | Zimmermann et al. |
| 6,096,309 A | 8/2000 | Prior et al. |
| 6,117,425 A | 9/2000 | MacPhee et al. |
| 6,123,655 A * | 9/2000 | Fell ............................. 494/50 |
| 6,153,113 A | 11/2000 | Goodrich et al. |
| 6,196,987 B1 | 3/2001 | Holmes et al. |
| 6,197,325 B1 | 3/2001 | MacPhee et al. |
| 6,200,287 B1 | 3/2001 | Keller et al. |
| 6,214,338 B1 | 4/2001 | Antanavich et al. |
| 6,245,900 B1 | 6/2001 | Yamasaki et al. |
| 6,280,400 B1 | 8/2001 | Niermann |
| 6,296,602 B1 | 10/2001 | Headley |
| 6,398,972 B1 | 6/2002 | Blasetti et al. |
| 6,406,671 B1 | 6/2002 | DiCesare et al. |
| 6,410,334 B1 * | 6/2002 | Schmolz ...................... 436/63 |
| 6,508,778 B1 | 1/2003 | Verkaart et al. |
| 6,516,953 B1 | 2/2003 | DiCesare et al. |
| 2001/0009757 A1 | 7/2001 | Bischof et al. |
| 2002/0104808 A1 | 8/2002 | Blasetti et al. |

FOREIGN PATENT DOCUMENTS

| | | |
|---|---|---|
| EP | 0 417 818 | 9/1990 |
| EP | 1005910 | 6/2000 |
| WO | 00/61256 | 10/2000 |
| WO | 01 03756 | 1/2001 |
| WO | 01/83068 | 11/2001 |
| WO | 03/015800 | 8/2002 |
| WO | 03/088905 | 4/2003 |

OTHER PUBLICATIONS

Symphony II Platelet Concentrate System/PCS Brochure; DePuy (Jan. 2003).

International Search Report; PCT/US03/16506; mailed Oct. 13, 2003.

Coller et al., The pH Dependence of Quantitative Ristocetin-induced Platelet Aggregation: Theoretical and Practical Implications—A New Device for Maintenance of Platelet-Rich Plasma pH, Blood, vol. 47, No. 5 (May), 1976.

Harvest®, SmpartPRep®PRP-20 Procedure Pack, "Instructions for Use".

* cited by examiner

APPARATUS AND METHOD FOR SEPARATING AND CONCENTRATING FLUIDS CONTAINING MULTIPLE COMPONENTS

CROSS-REFERENCE TO RELATED APPLICATIONS

This application claims the benefit of U.S. Provisional Application No. 60/383,013, filed on May 24, 2002. The disclosure of the above application is incorporated herein by reference.

FIELD

The present invention relates to a multiple component fluid and a concentrator/separator, and more particularly relates to a container operable with a centrifuge to separate and concentrate various biological components.

BACKGROUND

In the medical sciences, it is generally known to separate blood or various other biological fluids into their constituent parts, also referred to as fractions or phases. For example, whole blood samples include a plurality of constituents which may be separated by density in a device such as a centrifuge. The whole blood sample may be placed in a test tube, or other similar device, which is then spun in a centrifuge. In the centrifuge the whole blood is separated into different fractions depending upon the density of that fraction. The centrifugal force separates the blood sample into different fractions. In addition, various elements may be added to the test tube to create more than two fractions. In particular, commonly used gels may be used to divide the whole blood into a plurality of different fractions which may include fractions such as platelets, red blood cells, and plasma. Various other biological fluids may be separated as well. For example, nucleated cells may be separated and extracted from bone marrow or adipose tissue sample.

Many of these systems, however, do not provide a simple or efficient method to extract any more than one fraction and especially a fraction other than the top fraction. The top fraction of whole blood is plasma, or other blood constituents suspended in plasma. Thus, to extract other fractions the plasma fraction must either be removed or spun again to obtain the constituents suspended in this plasma. It is difficult to pierce the top fraction without co-mingling the sample. Accordingly, obtaining the other fractions is difficult with commonly known systems.

Other systems have attempted to alleviate this problem by providing a float or other device that is disposed within the sample at the interfaces of the different fractions during the centrifuge process. Nevertheless, these systems still do not allow a simple way to remove the different fractions without remixing the sample fractions. In addition, many of the systems do not allow an easy and reproducible method to remove the desired sample fraction.

Therefore, it is desired to provide a device to allow for the easy and reproducible removal of a particular fraction which does not happen to be the top fraction of a sample. It is desired to remove the required sample without mixing the different fractions during the extraction process. In addition, it is desired to provide a device which allows for a consistent extraction which includes known volumes or concentration of the fraction elements. Moreover, it is desired to separate and concentrate a selected fraction with one centrifuge step.

SUMMARY

An apparatus that separates and concentrates a selected fraction or component of a fluid, such as a biological fluid. For example, a buffy coat or platelet fraction or component of a whole blood sample or an undifferentiated cell component of bone marrow or adipose tissue sample. The apparatus, when used with a centrifuge, is generally able to create at least two fractions. It also provides for a new method of extracting the buffy coat fraction or component or middle fraction from a sample.

The apparatus includes a container to be placed in a centrifuge after being filled with a sample. A buoy or fraction separator, having a selected density less than one fraction but greater than a second fraction, is disposed in the container. During the centrifuge processing, the buoy is forced away from a bottom of the container as the denser fraction collects at the bottom of the container. The buoy is generally able to physically separate the denser fraction from another fraction of the sample.

After the centrifuge processing is finished, a piston or plunger is used to separate one of the fractions into at least two fractions. If whole blood is the sample, the plunger can separate the plasma fraction into a plasma fraction and a buffy coat. Then, at least one of the two fractions, formed with the plunger, may be removed from the container without substantially co-mingling the fractions of the sample. In whole blood, the buffy coat may be diluted or mixed with a selected volume of plasma.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following description exemplary refers to a blood separation, it will be understood that the present invention may be used to separate and concentrate any appropriate material. It will be further understood that many multi-component or multi-fraction fluids may be separated. The components or fractions are generally inter-mingled in the whole sample but may be separated with a centrifuge device that causes increased local gravity or gravitational forces.

Figure 1:
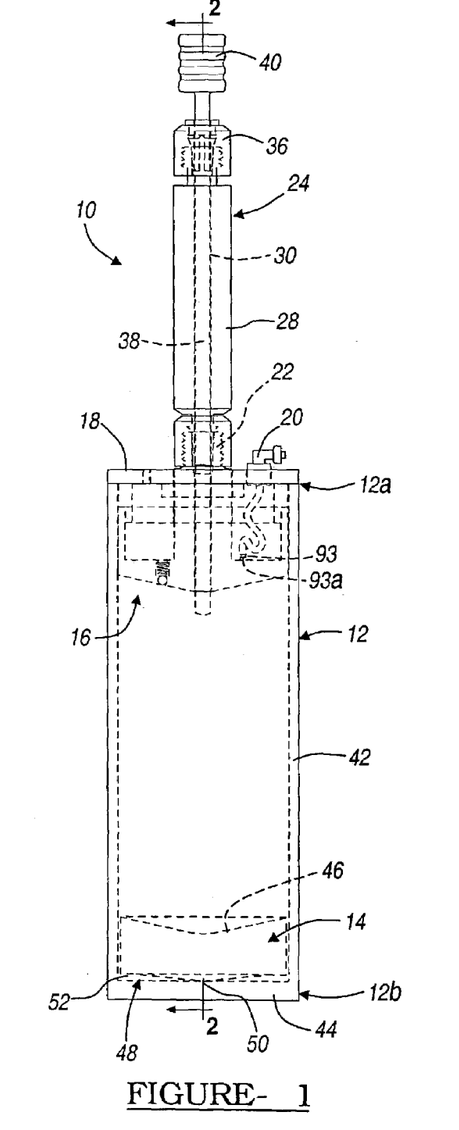
FIG. 1 is a plan view of a separator including a depth gage affixed to a plunger in a tube according to a first embodiment of the present invention.
Figure 2:
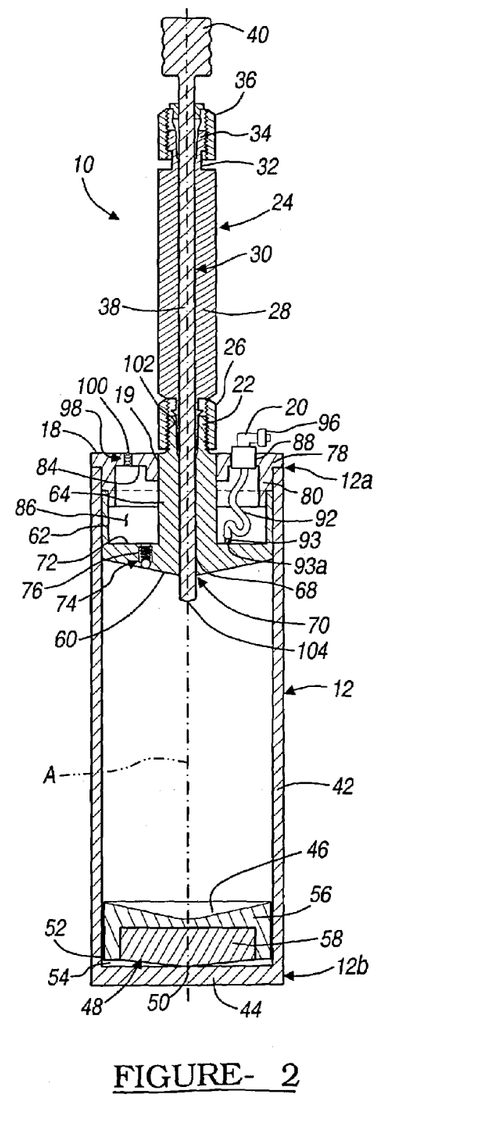
FIG. 2 is a cross-section view taken along line 2—2 of FIG. 1.
Figure 3:
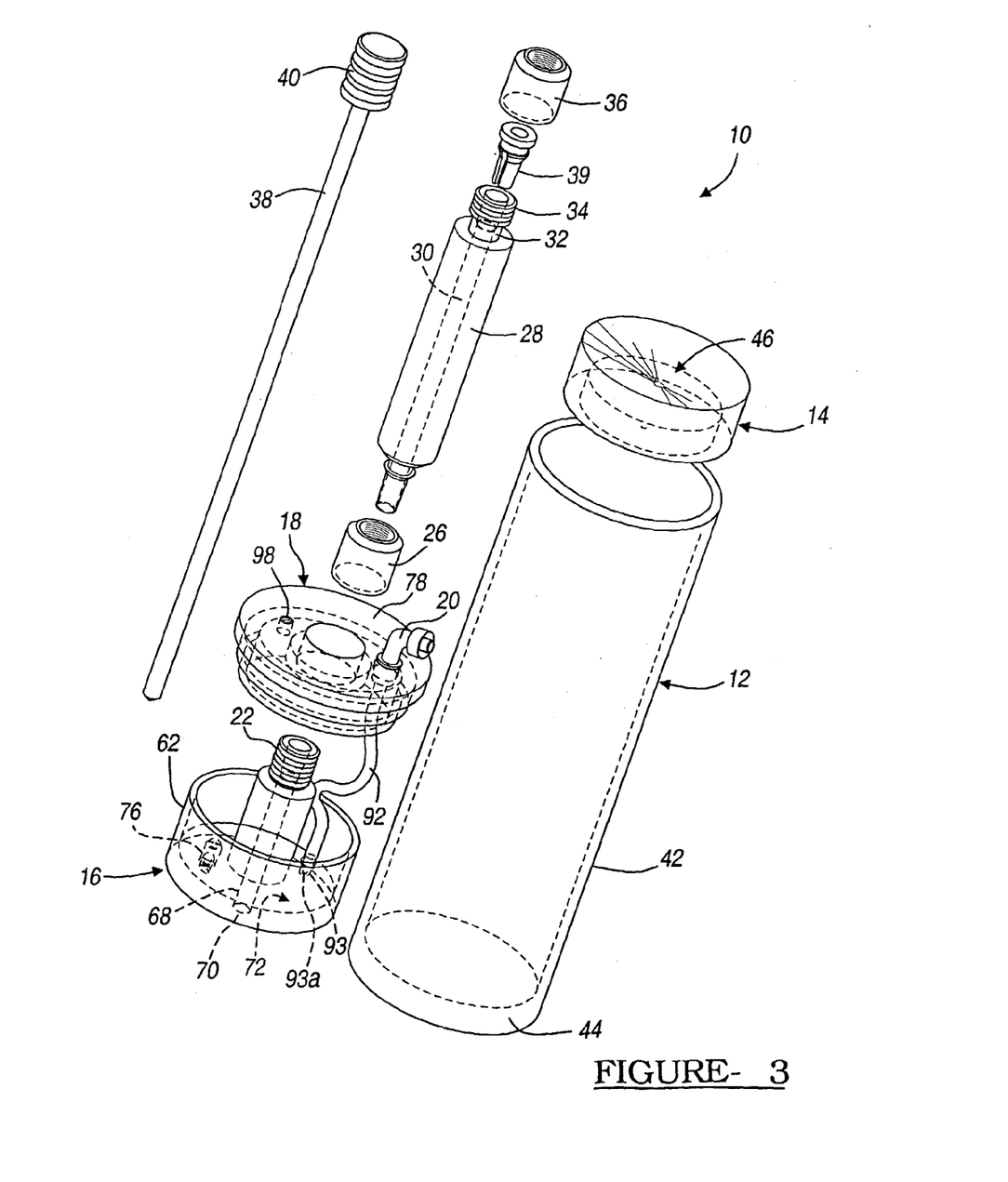
FIG. 3 is an exploded of the separator apparatus.

With reference to FIGS. 1–3, a separator 10, also referred to as a concentrator, is illustrated according to a first embodiment of the present invention. The separator 10 generally includes a tube or container 12 that is adapted to hold a fluid sample, such as an anti-coagulated whole blood sample, for further processing. It will be understood that the tube may hold other solutions including constituents of more than one density, such as bone marrow or a mixture of whole blood and bone marrow. The tube 12 includes a top or open end 12a, which is closeable, and a bottom or closed end 12b. The bottom 12c may also be selectively closeable.

Disposed within the tube 12 is a first piston or buoy 14 that is able to move along a central axis A of the tube 12. The buoy 14 is generally nearer the bottom end 12b of the tube 12 rather than the open end 12a. Also disposed within the tube 12 is a second piston or plunger 16. The plunger 16 is also able to move within the tube 12 generally between a position closer to the open end 12a to a position closer to the closed end 12b of the tube 12. A cap 18 substantially mates with the open end 12a of the tube 12 to close the tube 12 save for ports formed in the cap 18. Extending from the cap 18 is a plasma valve or port 20 that communicates with an area, described further herein, within the tube 12 defined between the plunger 16 and the cap 18. It will be understood that the plasma port 20 is merely exemplary in nature and simply allows for removal of a selected fraction of a sample, such as plasma from whole blood.

The cap 18 also includes a depth gage port 19. Extending from the plunger 16 and through the depth gage port 19 is a first plunger port 22. A depth guide or gage 24 includes a female connector 26 adapted to connect with the first plunger port 22. The depth gage 24 also includes a depth gage housing or cannula 28. The depth gage housing 28 defines a depth gage bore 30. Incorporated in the housing 28 and extending distal from the end mating with the plunger is a neck 32. The neck 32 includes external neck threads 34. The external neck threads 34 are adapted to engage appropriate internal threads of a mating member.

The mating member may include a compression nut 36 that mates with the external neck threads 34 to lock a depth gage rod 38 in a predetermined position. A split bushing 39 is also provided to substantially seal the depth gage housing 28 when the depth gage rod 38 is locked in place. The depth gage rod 38 extends through the depth gage housing 28 and terminates at a rod handle 40. The rod handle 40 may be a form easily manipulated by a human operator. The rod 38 extends coaxially with axis A of the tube 12. The depth gage rod 38 extends through the plunger 16 a predetermined distance and may be locked at that distance with the compression nut 36.

Although the tube 12 is described here as a cylinder, it will be understood that other shapes may be used, such as polygons. The internal portions, such as the cap 18, buoy 14, and plunger 16, would also include this alternate shape. Preferably the tube 12 is formed of a thermal plastic material which is flexible under the forces required to separate blood. The tube 12 may be made of a material that includes the properties of both lipid and alcohol resistance. These properties help increase the separation speed and decrease the amount of material which may cling to the tube wall 42. For example, Cyrolite MED2® produced by Cyro Industries of Rockaway, N.J. may be used to produce the tube 12.

The tube 12 has a tube wall 42 with a thickness of between about 0.01 millimeters and about 30.0 millimeters, although the tube wall 42 may be any appropriate thickness. The thickness of the tube wall 42 allows the tube wall 42 to flex during the centrifuge process yet be rigid enough for further processing of a blood sample disposed in the tube 12. The tube 12 is closed at the bottom end 12b with a tube bottom 44 formed of the same material as the tube wall 42 and is formed integrally therewith. Generally the tube bottom 44 has a thickness which is substantially rigid under the forces required to separate the sample such that it does not flex.

The buoy 14 includes an upper or collection face 46 that defines an inverse cone or concave surface. Generally the cone has an angle of between about 0.5° and about 45°, wherein the apex of the cone is within the buoy 14. The collection face 46 forms a depression in the buoy 14 which collects and concentrates material during the separation process. Additionally, the buoy 14 has a bottom face 48 that defines an inverse cone, dome, or covered surface. The buoy bottom face 48 includes an apex 50 that engages the tube bottom 44 before a buoy edge 52 engages the tube bottom 44. The buoy 14 includes a material that is a substantially rigid such that the buoy edges 52 never meet the tube bottom 44. Therefore, there is a gap or free space 54 formed between the buoy edge 52 and the tube bottom 44 along the perimeter of the buoy 14.

The separator 10 is generally provided to separate a multi-component fluid, that generally includes various components or constituents of varying densities that are co-mingled or mixed together. The separator 10 includes the buoy 14 that is of a selected density depending upon a selected constituent of the multi-constituent liquid. Although the buoy 14 may be tuned or of any selected density, the following example relates to separation of whole blood to various components. Therefore, the buoy 14 will be discussed to include a selected density relative to whole blood separation. It will be understood, however, that the buoy 14 may be of any appropriate density depending upon the multi-component fluid being separated.

The buoy 14 may be formed of any appropriate material that may have a selected density. For example, when the separator 10 is to separate blood, the buoy 14 generally has a density which is greater than that of red blood cells in a whole blood sample, but less than the plasma or non-red blood cell fraction of a whole blood sample. For blood, the density of the buoy 14 is generally between about 1.02 g/cc and about 1.09 g/cc.

To achieve the selected density, the buoy 14 may be formed as a composite, or multi-piece construction, including a plurality of materials. Particularly, a first or outside portion 56 defines the collection face or surface 46 and the buoy edge 52 and is formed of the same material as the tube 12. The outside portion 56 defines a cup or void into which a plug or insert 58 is placed. The insert 58 has a mass such that the density of the entire buoy 14 is within the selected range, for example the range described above. Generally, a high density polyethylene may be used, but the material and size of the insert 58 may be altered to produce the desired density of the buoy 14. Alternatively, the buoy 14 may be formed of a single suitable material that has a density in the selected range. Nevertheless, the buoy 14 formed unitarily or of a single material would still include the other portions described in conjunction with the buoy 14.

The outside portion 56 of the buoy 14 also defines the outside circumference of the buoy 14. The outside circumference of the buoy 14 is very close to the internal circumference of the tube 12. Due to the operation of the buoy 14, however, described further herein, there is a slight gap between the outside of the buoy 14 and the inside of the tube 12. Generally, this gap is between about 1 and about 10 thousandths of an inch around the entire circumference of the buoy 14. Generally, it is desired that the distance between the outside circumference of the buoy 14 and the inside circumference of the tube 12 is great enough to allow a selected material or component to pass. For example, in whole blood the distance is selected so that red blood cells may pass through the gap without being lysed, damaged, or activated.

The plunger 16 includes a plunger front or collection face 60 and a plunger wall 62 that extends from the plunger front face 60. The plunger wall 62 extends relatively perpendicular to the plunger front face 60 and substantially parallel to the tube wall 42. Extending from the center of the plunger 16 is a sample collection projection 64. Extending from the top of the collection projection 64 is the first plunger port 22. The sample collection projection 64 includes a plunger sample collection bore 68 defined therethrough. The plunger sample collection bore 68 terminates at a sample collection aperture 70 that is substantially in the center of the plunger front face 60. The plunger front face 60 also defines an inverse cone where the sample collection aperture 70 is the apex of the cone. The plunger front face 60 defines a cone with an angle substantially similar to the collection face 46 of the buoy 14. In this way, the plunger front face 60 may mate substantially completely with the collection face 46 for reasons described more fully herein.

The plunger 16 also includes a back face 72. Extending from the plunger front face 60 to the back face 72 is a bore 74. A check valve 76 is operably connected to the bore 74. The check valve 76 allows a liquid to move from the plunger front face 60 to the back face 72 while not allowing the liquid to move from the back face 72 to the plunger front face 60. Therefore, the check valve 76 is substantially a one-way valve which allows a material to move in only one direction. The check valve 76 may also operate automatically allowing flow in only one predetermined direction. Alternatively, the check valve 76 may be operated manually and include a portion extending from the check valve 76 requiring manipulation to stop or start a flow through the check valve 76.

The plunger 16 may be made out of any appropriate material which does not interfere with the separation of the fractions of the fluid, such as whole blood. The plunger 16, however, is made of a material that is flexible or at least partially deformable. A flexible material allows the plunger 16 to have an external circumference defined by the plunger walls 62 that is substantially equal to the internal circumference of the tube 12. Because of the deformability of the plunger 16, however, the plunger 16 is still able to move within the tube 12. The plunger 16 is able to move through the tube 12 and also substantially wipe the interior of the tube wall 42. This creates, generally, a moveable seal within the tube 12. Thus, substantially no material escapes the action of the separator 10 when the plunger 16 is plunged into the tube 12. This also helps concentrate the portion of the sample desired to be collected, described more fully herein.

The cap 18 provides a structure to substantially close the tube 12. The cap 18 particularly includes a plate 78 that has an external circumference substantially equal to the external circumference of the tube 12. Extending from the plate 78 and into the tube 12 is a flange 80. The external circumference of the flange 80 is substantially equal to the internal circumference of the tube 12. In this way, the cap 18 substantially closes the tube 12. It will be understood the cap 18 may be in any form so long as the cap 18 substantially closes and/or seals the tube 12 when installed.

Formed through the center of the plate 78 is the depth gage port 19. The depth gage port 19 is also adapted to receive the sample collection projection 64. The first plunger port 22 extends above the plate 78 through the depth gage port 19. The circumference of the depth gage port 19 is substantially equal to the external circumference of the sample collection projection 64 such that a liquid seal is formed. The plate 78 defines a sample face 84 that includes an interior side of the cap 18. The area between the sample face 84 of the cap 18 and the back face 72 of the plunger 16 define a plasma collection area 86. Although the plasma collection area 86 is exemplary called the plasma collection area, it will be understood that the plasma collection area 86 may also collect any appropriate fraction of the sample that is positioned within a separator 10. The plasma collection area 86 is merely an exemplary name and an example of what material may be collected in the area of the separator 10. As discussed herein, the separator 10 may used to separate whole blood into various fractions, therefore the plasma collection area 86 is used to collect plasma. The plasma collection area 86 also allows a space for the check valve 76 to be installed.

A second bore 88 is formed in the plate 78. Extending through the second bore 88 is the plasma collection valve 20. In liquid communication with the plasma collection valve 20 is a plasma collection tube 92. The plasma collection tube 92 has a length such that the plasma collection tube 92 is able to extend from the plasma collection valve 20 to substantially the tube bottom 44. The plasma collection tube 92, however, is flexible enough such that it may be folded or compressed to fit within the plasma collection area 86 when the plunger is substantially near the top 12a of the tube 12. The plasma collection tube 92 may also be connected to a hose barb 93 that includes a plasma collection bore 93a. The plasma collection bore 93a is substantially level with the plunger back face 72. Alternatively, the plasma collection bore 93a may be positioned below the plunger back face 72 but in fluid communication with the plasma collection tube 92.

The outboard side of the plasma collection valve 20 may include external threads 94 to mate with internal threads of a plasma valve cap 96. Therefore, the plasma collection valve 20 may be selectively opened and closed via the plasma valve cap 96. It will be understood, however, that other appropriate means may be used to open and close the plasma collection valve 20 such as a clip or a plug. It will be understood that the plasma collection valve 20, plasma collection tube 92, plasma collection bore 23a may be used to collect any appropriate material or fraction from the separator 10.

Also formed in the plate 78 is a vent bore 98. The vent bore 98 allows air to flow into the collection area 86 as the plunger 16 is being plunged into the tube 12. The vent bore 98 may include a filter 100 such that liquid cannot escape from the tube 12. The filter 100 allows air to enter or escape from the collection area 86 while maintaining the liquid seal of the tube 12 produced by the cap 18.

Selectively attachable to the first plunger port 22 is the depth gage 24. The female connector 26 interconnects the depth gage housing 28 to the first plunger port 22. Internal threads in the female connector 26 mate with an external thread 102 formed on the first plunger port 22. It will be understood, however, that other engagement mechanisms between the depth gage 24 and the plunger 16 may be used. For example, a snap connection rather than a threaded connection between the two may be used.

The depth gage housing 28 is formed to be substantially rigid. Suitable materials, when sized properly, include polycarbonate and CYRO MED2®. The material preferably is both rigid and does not substantially react with the sample. It is rigid enough to provide a mechanism to plunge the plunger 16 into the tube 12. In addition the external circumference of the depth gage housing 28 is substantially equal to the circumference of the depth gage port 19 in the plate 78. Therefore, as the plunger 16 is being plunged into the tube 12 with the depth gage 24, no liquid material is allowed to escape around the depth gage housing 28 and through depth gage port 19.

Formed within the depth gage housing 28 is the bore 30 which receives the depth gage rod 38. The depth gage rod 38 extends through the sample collection bore 68 of the sample collection projection 64 and protrudes through the sample collection aperture 70 a predetermined length. The depth gage rod 38 extends through the sample collection aperture 70 a length such that when an end 104 of the depth gage rod 38 meets the buoy 14, the volume defined by the collection face 46 and the plunger front face 60 is between about 5 percent and about 30 percent of the total volume of the sample that the tube 12 holds. The projection of the depth gage rod 38 allows for an easily reproducible collection amount and concentration over several trials.

The compression nut 36 locks the depth gage rod 38 in the predetermined position. Nevertheless, once the plunger 16 has been plunged to the desired depth in the tube 12, the compression nut 36 may be loosened so that the depth gage rod 38 may be removed from the plunger 16 and the depth gage housing 28 without moving the plunger 16. A syringe or other appropriate device may then be affixed to the external neck threads 34 of the depth gage 24 to extract the fraction or phase that is between the plunger front face 60 and the collection face 46. As described further herein, the fraction or phase that is left between the plunger front face 60 and the collection face 46 may be the buffy coat of a whole blood sample. Nevertheless, it will be understood that the fraction between the plunger front face 60 and the collection face 46 may be any appropriate fraction of the sample that is disposed in the separator 10.

Figure 4:
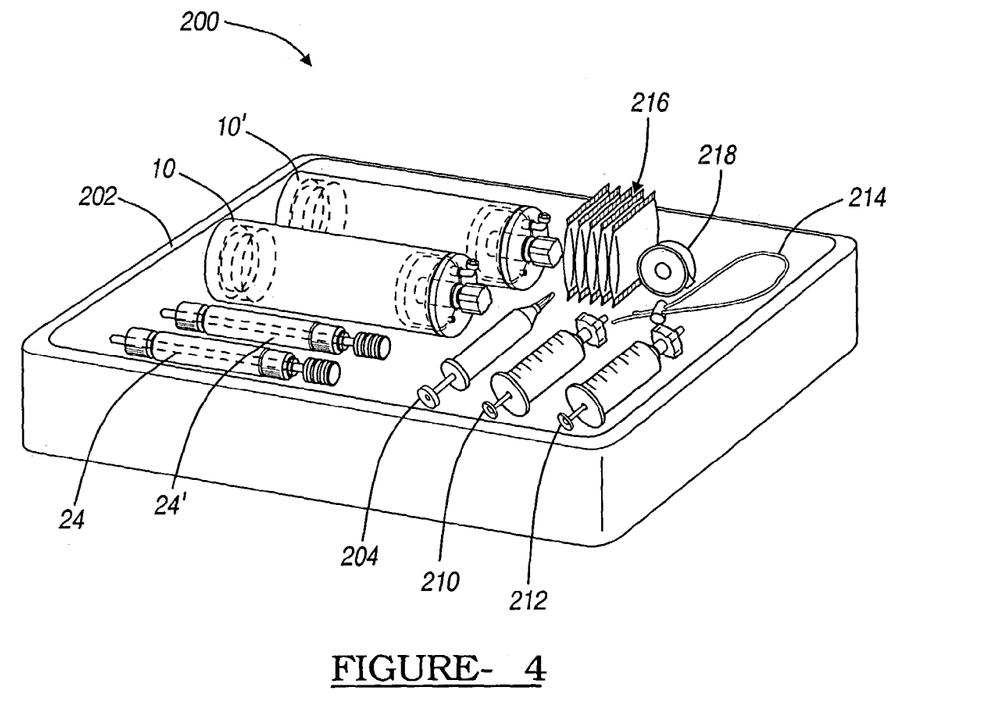
FIG. 4 is a kit including the separator according to an embodiment of the present invention.

The separator 10 may be provided alone or in a kit 200, as illustrated in FIG. 4. The kit 200 may be placed in a tray 202 which is covered to provide a clean or sterile environment for the contents of the kit 200. The kit 200 may include at least a first separator 10 and a second separator 10'. A first depth gage 24 and a second depth gage 24' are also provided, one for each separator 10, 10'. The kit 200 also generally includes a first syringe 204, including a needle, to draw a biological sample, such as blood from a patient. The first syringe 204 may also be used to place the sample in the first separator 10. After centrifuging the sample a second device or syringe 210 may be used to extract a first fraction of the sample. While a third device or syringe 212 may be used to extract a second fraction of the sample. Also a turnicate 214 and other medical supplies, such as gauze 216 and tape 218, may be provided to assist the practitioner. It will be understood the elements of the kit 200 are merely exemplary and other appropriate items or elements may be included.

With reference to FIGS. 5A–5D a method using the blood separator 10 is illustrated. The following example relates specifically to the taking and separation of a sample of whole blood from a patient. Nevertheless, it will be understood that another appropriate biological material may be separated and concentrated using the separator 10. For example, bone marrow may be separated and concentrated using the separator 10. The various fractions of the bone marrow are similar to the fractions of whole blood. Generally, the bone marrow includes a fraction that includes substantially dense material and a second phase that is less dense and has other components suspended therein, such as nucleated cells. The bone marrow sample may be positioned in the separator 10, similarly to the whole blood as described herein, and separated in a substantially similar manner as the whole blood. The separator 10 can then be used to remove nucleated cells from the bone marrow sample whereas the separator 10, as described herein, is used to remove the buffy coat from the whole blood which includes platelets and other appropriate materials.

A mixture of whole blood and bone marrow may be positioned in the separator 10 for separation and concentration. Similar methods and steps will be used to separate the mixture of whole blood and bone marrow with a main difference being the material that is separated. It will also be understood that various centrifuge times or forces may be altered depending upon the exact material that is being separated with the separator 10. It will also be understood that the separation of whole blood, bone marrow, or a mixture of whole blood and bone marrow are merely exemplary of the materials that may be separated using the separator 10.

With reference to FIGS. 5A–5D and to a whole blood sample, a sample of whole blood taken from a patient is placed in the tube 12 with an anticoagulant using the first syringe 204 or other appropriate delivery method. In particular, the first syringe 204 may be connected to the first plunger port 22. After which the blood sample is provided to the tube 12 via the sample collection bore 68 and sample collection aperture 70. A cap 220 is then placed over the first plunger port 22 to substantially seal the tube 12.

Figure 5A:
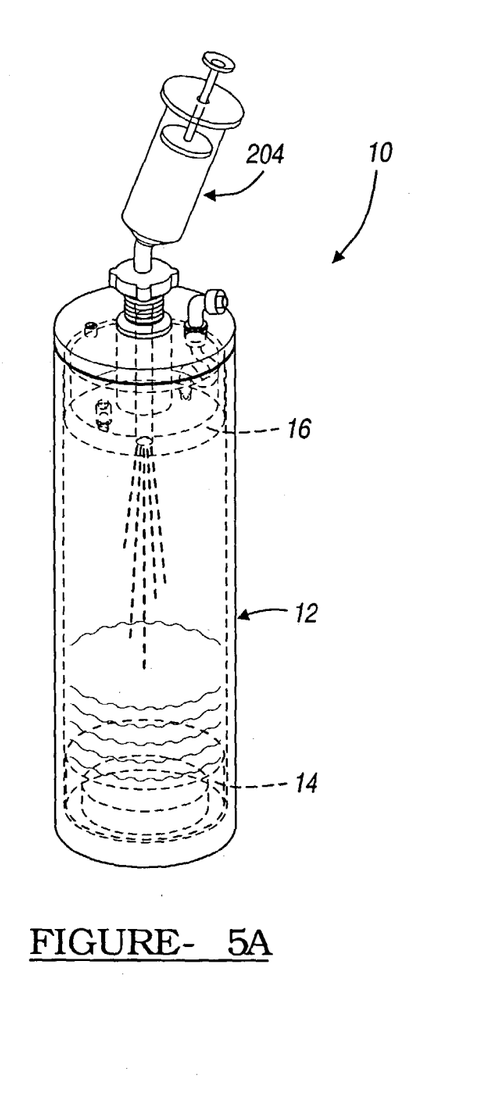
FIG. 5A is a plan view of the separator being filled.

After the whole blood sample is delivered to the tube 12, the separator 10 is placed in a centrifuge. The second separator 10', substantially identical to the first, is placed opposite the first separator 10 including the sample in a centrifuge. The second separator 10' may also include a second sample or may include a blank, such as water, so that the centrifuge is balanced. The second separator 10' balances the centrifuge, both by weight and dynamics.

Figure 5B:
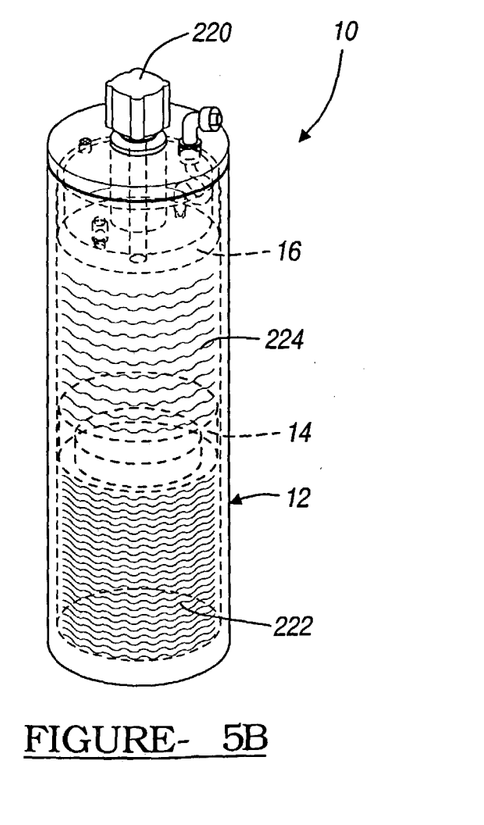
FIG. 5B is a plan view of a blood sample in the separator after the centrifuge process.

The separator 10 is then spun in the centrifuge in a range between about 1,000 and about 8,000 RPMs. This produces a force between about 65 and about 4500 times greater than the force of normal gravity, as generally calculated in the art, on the separator 10 and the blood sample placed in the separator 10. At this force, the more dense material in a whole blood sample is forced towards the bottom 12b of the tube 12. The dense material, such as red blood cells or a red blood cell fraction 222, collects on the tube bottom 44. Because the buoy 14 has a density that is less than the red blood cell fraction 222, it is forced in a direction toward the top 12a of the tube 12 in the centrifuge. Nevertheless, because the buoy 14 is denser than a plasma fraction 224, the buoy 14 does not reach the top 12a of the tube 12.

The forces also affect the tube wall 42. The forces compress the tube 12 linearly along axis A thereby bowing or flexing the tube wall 42. As the tube wall 42 compresses it increases the diameter of the tube 12 making it easier for the buoy 14 to move in the direction of the top 12a of the tube 12. In addition, the bottom face 48, defining an inverse cone, helps the initial movement of the buoy 14. Because the buoy 14 is not substantially flat along its bottom, it does not form a vacuum interaction with the tube bottom 44. Therefore, the initial movement of the buoy 14 away from the tube bottom 44 is quicker than if the bottom of the buoy 14 was flat.

During the centrifuge process the red bloods cells of the red blood cell fraction 222 force the buoy 14 in the direction of the top 12a of the tube 12 because the buoy 14 is less dense than the red blood cell fraction 222. Although the whole blood sample, including the red blood cells is loaded above the buoy 14, the red blood cells are able to move between the buoy 14 and the tube wall 42 because the circumference of the buoy 14 is less than the internal circumference of the tube 12. During the centrifuge process the buoy 14 stops at an interface of a plasma fraction 224 and the red blood cell fraction 222 because of the selected or tuned density of the buoy 14.

With particular reference to FIG. 5B, the centrifuge process has been completed and the buoy 14 has moved to the interface of the red blood cell fraction 222 and plasma fraction 224. After the tube 12 has been removed from the centrifuge, the tube wall 42 decompresses which helps support the buoy 14 at the interface position. It is also understood that applying an external pressure to the tube 12 via fingers or another apparatus may help stabilize the buoy 14 during the plunging procedure described herein.

On or near collection face 46 is a third fraction 226 including a small, yet concentrated, amount of red blood cells, white blood cells, platelets, and a substantial portion of a buffy coat of the blood sample. Although the plasma is also present near the collection face 46 at this point the solid portions of the buffy coat are more compressed against the collection face 46. The position of the buoy 14 also helps in this matter. Because the buoy 14 is a single body it defines the interface of the plasma traction 224 and the red blood cell fraction 222. Also the density of the buoy 14 assures that it has not passed into the plasma fraction 224. Therefore, the fractions remain separated after the centrifuge process. In addition because the buoy 14 is tuned to the density of the red blood cell fraction 222, it is not affected by variations in the density of the plasma fraction 224 and the buoy's 14 position is always at the interface of the red blood cell fraction 222 and the plasma fraction 224.

Figure 5C:
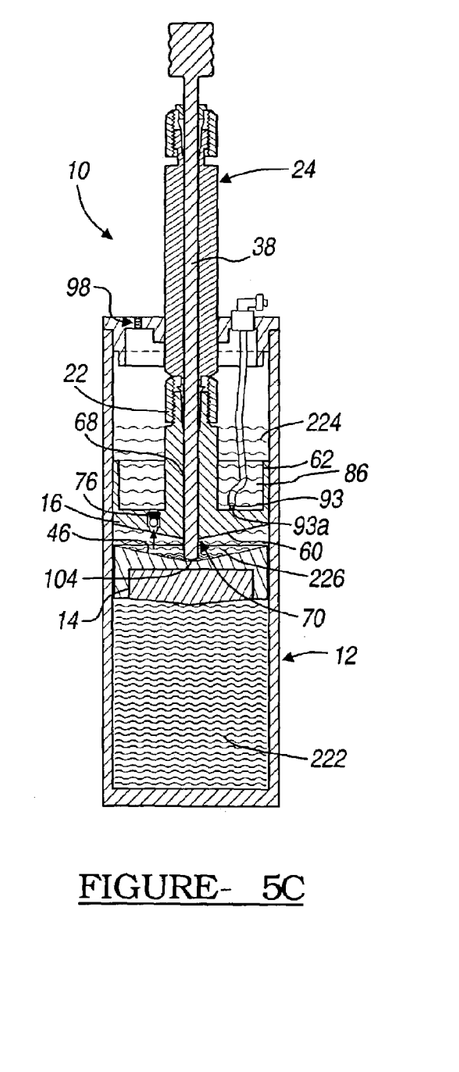
FIG. 5C is a plan view of the plunger plunged into the tube with the depth gage to further separate the blood sample.

With particular reference to FIG. 5C, the depth gage 24 is affixed to the first plunger port 22 of the sample collection projection 64. After connecting the depth gage 24 to the first plunger port 22, the plunger 16 is plunged into the tube 12 by pushing on the depth gage 24. As this is performed the plasma fraction 224, formed and separated above the buoy 14, is able to flow through the check valve 76 into the plasma collection area 86. This displacement of the plasma fraction 224 allows the plunger 16 to be plunged into the tube 12 containing the blood sample.

The plunger 16 is plunged into the tube 12 until the point where the end 104 of the depth gage rod 38 reaches the buoy 14. The volume left in the collection face 46 is the third fraction 226 and is determined by the depth gage 24. It may be adjusted by selectively determining the amount that the depth gage rod 38 extends below the plunger front face 60. By adjusting the depth gage 24, the concentration of the third fraction 226 can be adjusted depending upon the desires of the operator.

The plasma fraction 224 is held in the plasma collection area 86 for later withdrawal. Therefore, the use of the plunger 16 and the buoy 14 creates three distinct fractions that may be removed from the tube 12 after only one spin procedure. The fractions include the red blood cell fraction 222, held between the buoy 14 and the tube bottom 44. The third or buffy coat fraction 226 is held between the plunger 16 and the buoy 14. Finally, the plasma fraction 224 is collected in the plasma collection area 86.

Figure 5D:
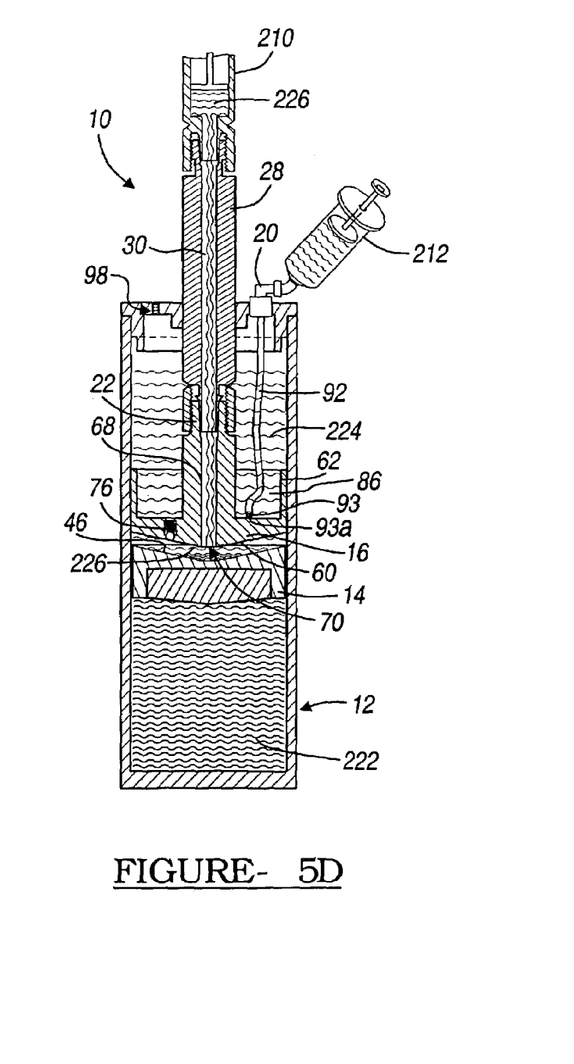
FIG. 5D is a plan view of the buffy coat and the plasma fractions being extracted from the separator.

The third fraction 226 may be extracted from the tube 12 first, without commingling the other fractions, through the sample collection bore 68. With particular reference to FIG. 5D, the depth gage rod 38 may be removed from the depth gage housing 28. This creates a sample collection cannula which includes the depth gage bore 30, the sample collection bore 68, and the sample collection aperture 70. After the depth gage rod 38 has been removed, the second syringe 210 may be affixed to the depth gage housing 28 via the external neck threads 34. The second syringe 210 may be substantially similar to the first syringe 204.

Before attempting to withdraw the third fraction 226 the separator 10 may be agitated to re-suspend of the platelets and concentrated red blood cells in a portion of the plasma remaining in the collection face 46. This allows for easier and more complete removal of the third fraction 226 because it is suspended rather than compressed against the collection face 46. A vacuum is then created in the second syringe 210 by pulling back the plunger to draw the third fraction 226 into the second syringe 210.

As the third fraction 226 is drawn into the second syringe 210 the plunger 16 moves towards the buoy 14. This action is allowed because of the vent bore 98 formed in the cap 18. Atmospheric air is transferred to the plasma collection area 86 through the vent bore 98 to allow the third fraction 226 to be removed. This also allows the movement of the plunger 16 towards the buoy 14. This action also allows the plunger 16 to "wipe" the collection face 46. As the plunger front face 60 mates with the collection area 46 the third fraction 226 is pushed into the sample collection aperture 70. This ensures that substantially the entire third fraction 226 collected in the collection area 46 is removed into the second syringe 210. It also increases the consistency of the collection volumes. In addition, because the second syringe 210 does not protrude out the sample collection aperture 70, it does not interfere with the collection of the third fraction 226. Once the plunger front face 60 has mated with the collection face 46 there is substantially no volume between the plunger 16 and the buoy 14.

Once the third fraction 226 is extracted the second syringe 210 is removed from the first plunger port 22. Also the extraction of the third fraction 226 leaves the plasma fraction 224 and the red blood cell fractions 222 separated in the tube 12. At this point a third syringe 212 may be affixed to the plasma collection valve 20. The third syringe 212 is connected to the external threads 94 of the plasma collection valve 20 to ensure a liquid tight connection. It will be understood, however, that another connection mechanism such as a snap or compression engagement may be used to connect the third syringe 212 to the plasma collection valve 20.

A vacuum is then created in the third syringe 212 to draw the plasma fraction 224 from the plasma collection area 86 through the plasma collection tube 92. As discussed above, the plasma collection tube 92 is connected to the hose barb 93. Therefore, the plasma flows through the plasma collection bore 93a through the hose barb 93, and then through the plasma collection tube 92. It will be understood that the plasma collection tube 92 may alternatively simply rest on the plunger back face 72 to collect the plasma fraction 224. In this way the plasma fraction 224 may be removed from the blood separator 10 without commingling it with the red blood cell fraction 222. After the plasma fraction 224 is removed, the separator 10 may be dismantled to remove the red blood cell fraction 222. Alternatively, the separator 10 may be discarded in an appropriate manner while retaining the red blood cell fraction 222.

The separator 10 allows for the collection of three of a whole blood sample's fractions with only one centrifugation spin. The interaction of the buoy 14 and the plunger 16 allows a collection of at least 40% of the available buffy coat in the whole blood sample after a centrifuge processing time of about 5 minutes to about 15 minutes. The complimentary geometry of the plunger front face 60 and the collection face 46 help increase the collection efficiency. Although only the cone geometry is discussed herein, it will be understood that various other geometries may be used with similar results.

The plunger front face 60 being flexible also helps ensure a complete mating with the collection face 46. This, in turn, helps ensure that substantially the entire volume between the two is evacuated. The process first begins with the suction withdrawal of the third fraction 226 via the second syringe 210, but is completed with a fluid force action of the third fraction 226 as the plunger front face 60 mates with the collection face 46. As the plunger front face 60 mates with the collection face 46 the fluid force assists in removal of the selected fraction.

The plunger 16 also substantially wipes the tube wall 42. Because the plunger 16 is formed of a flexible material it forms a seal with the tube wall 42 which is movable. Therefore, substantially no liquid is able to move between the plunger wall 62 and the tube wall 42. Material is substantially only able to go past the plunger front face 60 via the check valve 76.

The complimentary geometry also helps decrease the collection time of the third fraction 226. Therefore, entire time to prepare and remove the third fraction 226 is generally about 5 to about 40 minutes. This efficiency is also assisted by the fact that the separator 10 allows for the removal of the third fraction 226 without first removing the plasma fraction 224, which includes the buffy coat, and respinning the plasma fraction 224. Rather one spin in the separator 10 with the whole blood sample allows for the separation of the buffy coat for easy extraction through the plunger 16.

As discussed above, the separator 10 may be used to separate any appropriate multi-component material. For example, a bone marrow sample may be placed in the separator 10 to be centrifuged and separated using the separator 10. The bone marrow sample may include several fractions or components that are similar to whole blood fractions or may differ therefrom. Therefore, the buoy 14 may be altered to include a selected density that is dependent upon a density of a selected fraction of the bone marrow. The bone marrow may include a selected fraction that has a different density than another fraction and the buoy 14 may be designed to move to an interface between the two fractions to allow for a physical separation thereof. Similar to the whole blood fraction, the plunger 16 may then be moved to near a collection face 46 of the buoy 14. The fraction that is then defined by the collection face 46 and the plunger 16 may be withdrawn, as described for the removal of the buffy coat from the whole blood sample. For example, the middle fraction or third fraction in the bone marrow sample may include a fraction of undifferentiated or stem cells.

It will also be understood that mixtures of various fluids may be separated in the separator 10. For example, a mixture of whole blood and bone marrow may be positioned in the separator 10 at a single time. The buoy 14 may be tuned to move to a interface that will allow for easy removal of both the buffy coat, from the whole blood sample, and the undifferentiated cells, from the bone marrow sample. Nevertheless, it will be understood that the separator 10 may be used within any appropriate biological material or other material having multiple fractions or components therein. Simply, the buoy 14 may be tuned to the appropriate density and the plunger 16 may be used to cooperate with the buoy 14 to remove a selected fraction.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of separating a multi-component fluid using a centrifuge process and a container to hold the multi-component fluid during the centrifuge process, comprising:
    forming a first fraction and a second fraction by centrifuging the multi-component fluid disposed in the container;
    containing said second fraction in a collection area depression of a first piston with a selected volume of said first fraction; and
    withdrawing said second fraction and said selected volume of said first fraction from the container;
    wherein the collection area depression of the first piston has a cone within said first piston to define said collection area.

2. The method of claim 1, wherein forming a first fraction and a second fraction includes:
    positioning the container in a device able to create an artificial gravity higher than ambient gravity on the container in the multi-phase fluid contained in the container wherein centrifuging the multi-phase fluid creates said higher gravity;
    moving the first piston from a first position to a second position within the container via at least a density gradient of the fluid on the first piston; and
    substantially collecting the second fraction within the collection area of the first piston.

3. The method of claim 1, further comprising:
    disposing the first piston within the container before centrifuging the multi-phase liquid;
    wherein disposing the first piston includes providing the first piston with a collection face defining a selected volume for collecting said second fraction.

4. The method of claim 3, wherein providing the piston includes:
    generally forming a cone within said first piston to define said collection face;
    wherein said cone includes an apex within a body of said first piston.

5. The method of claim 3, further comprising:
    moving a second piston within the container;
    providing a second collection face on said second piston which is operable to substantially mate to the collection area of said first piston.

6. The method of claim 1, further comprising:
    forming a third fraction;
    wherein the first piston substantially separates said first fraction and said third fraction and generally containing said second fraction.

7. The method of claim 6, wherein containing said second fraction, further includes:
    moving a second piston from a first position to a second position closer to the collection area of the first piston, such that said second piston and said first piston define a volume substantially containing said second fraction and said selected volume of said first fraction.

8. The method of claim 1, further comprising:
selecting a geometry of the collection area of the first piston;
providing a second piston including a collection face having a geometry substantially complementary to said geometry of the collection area such that said collection face may substantially mate with said collection area such that there is generally no space between said collection face and said collection area of said first piston.

9. The method of claim 8, wherein withdrawing said second fraction includes:
moving the second piston towards said first piston to contain said second fraction and said selected volume of said first fraction;
wherein containing said second fraction and said selected volume of said first fraction includes providing a depth gage that engages said first piston when said second piston has contained the selected volume.

10. The method of claim 9, further comprising:
providing a passageway through a piston rod operably affixed to said second piston generally through said collection face and from said collection area of said first piston;
wherein withdrawing said second fraction includes creating a vacuum through said piston rod and removing said second fraction from said collection area.

11. The method of claim 10, further comprising:
generally suspending said second fraction in said selected volume of said first fraction such that a generally liquid phase is formed.

12. The method of claim 1, further comprising:
moving a second piston from a first position to a second position such that said second fraction is contained in a collection area and said first fraction is substantially contained in a first fraction collection area; and
withdrawing said first fraction from the container substantially independent of withdrawing said second fraction from said container.

13. The method of claim 12, wherein withdrawing said first fraction includes:
disposing a conduit in said first fraction collection area including a port to an exterior of the container; and
forming a vacuum exterior to the container to withdraw said first fraction from said first fraction collection area.

14. The method of claim 1, wherein withdrawing said second fraction includes:
moving a second piston through the container towards said first piston;
providing a selected geometry of said collection area of said first piston substantially complementary to a geometry of a collection face of said second piston;
producing a fluid force of the liquid phase material by substantially compressing said collection face within said collection area of said first piston.

15. The method of claim 1, wherein forming a second fraction generally within said collection area by centrifuging the multi-phase liquid is performed in less than about ten minutes.

16. The method of claim 1, further comprising:
forming a third fraction; and
providing said first piston with a selected density such that is able to substantially automatically reach an interface of said first fraction and said third fraction of the multi-phase fluid during the centrifuge process.

17. The method of claim 16, wherein said selected density is generally above 1.0 g/cc to about 1.1 g/cc.

18. The method of claim 1, further comprising:
substantially separating the first fraction and the second fraction with the first piston from a third fraction;
wherein the first piston moves to a position substantially between the first fraction and the second fraction to separate the first fraction and the second fraction.

19. The method of claim 18, further comprising:
providing a second piston and a piston rod;
moving the second piston via the piston rod through a volume of the first fraction to a position near the first piston after the first piston has separated the first fraction and the second fraction to define a volume including a portion of the first fraction and the second fraction.

20. The method of claim 19, further comprising:
withdrawing the volume including the second fraction and the portion of the first fraction without removing the remaining portions of the first fraction.

21. A system for separating a multi-component fluid with centrifugation, the system comprising:
a container, having a bottom and a side wall extending from said bottom, defining a sample holding area; and
a first piston disposed in said sample holding area; and
a member to selectively close a top of said container;
wherein said first piston is movable when acted upon by forces created during the centrifugation;
wherein said first piston defines a collection surface sump for collecting a selected component of the multi-component fluid.

22. The system of claim 21, wherein said first piston generally includes a side that terminates at a plane;
wherein said collection surface extends into said first piston.

23. The system of claim 22, wherein said collection surface generally defines a cone extending from a plane defined by said first piston and having an apex within said first piston.

24. The system of claim 23, wherein said cone includes an angle less than about 70°.

25. The system of claim 21, further comprising:
a second piston moveable within said sample holding area having a collection face;
wherein said second piston is moveable from a first position to a second position generally closer to said collection surface of said first piston;
wherein said collection face of said second piston is substantially complementary to said collection surface of said first piston.

26. The system of claim 21, wherein said first piston includes a wall generally terminating in a second plane;
wherein a surface of said piston extends from said second plane in a generally tapering fashion.

27. The system of claim 26, wherein said surface of said first piston is at least one of substantially convex and extends towards an apex from said second plane.

28. The system of claim 26, wherein said surface extending from said second plane generally eliminates a substantial mating of said second surface and said bottom of said container.

29. The system of claim 21, wherein said first piston is formed of a material that is substantially inert relative to biological components.

30. The system of claim 21, wherein said first piston includes a selected density such that said first piston is able to achieve a selected position between two components of a multi-component fluid during the centrifugation.

31. The system of claim 30, wherein said selected density is achieved by forming said first piston from a first material and a second material.

32. A system for separating a multi-component fluid with a centrifuge, comprising:
a container including a bottom and a side wall extending from said bottom;
a first piston moveable within said sample holding area defining a collection area with a depression defined by the first piston;
a second piston operably connected to a piston rod, said second piston defining a collection face projection;
wherein said collection area and said collection face are substantially mateable;
wherein said container generally defines a sample holding area;
wherein said second piston is disposable and moveable within said sample holding area.

33. The system of claim 32, wherein said collection area generally defines a concave cone having an apex substantially within said first piston.

34. The system of claim 33, wherein said inverse cone generally includes an angle of about 0.5° and about 45°.

35. The system of claim 32, wherein said collection face generally defines a convex cone having an apex generally outside said second piston.

36. The system of claim 35, wherein the convex cone generally includes an angle of about 0.5° to about 45°.

37. The system of claim 32, wherein said collection area generally defines a concave area substantially within said first piston;
wherein said second collection face generally defines a convex surface extending from said second piston;
wherein said collection area and said collection face are generally mateable to substantially eliminate any volume between said collection area and said collection face.

38. The system of claim 32, wherein said second piston is formed of a material that is substantially inert to biological components.

39. The system of claim 32, wherein an exterior dimension of said second piston is substantially equal to a dimension of said sample holding area, wherein as second piston is moved within said sample holding area said second piston is able to substantially produce a moving seal within said sample holding area.

40. The system of claim 39, further comprising:
a check valve disposed in said second piston;
wherein said check valve allows a material to pass through said second piston as said second piston moveably seals said sample holding area.

41. The system of claim 32, further comprising:
a piston rod extending from said second piston;
wherein said piston rod defines a collection conduit;
wherein said collection area and said collection face initially define a collection volume to which said collection conduit communicates.

42. The system of claim 41, wherein material is removable from said collection volume through said collection conduit;
wherein said collection face is moveable towards said collection area as material is removed from said collection volume.

43. The system of claim 32, wherein said collection area and said collection face are able to form fluid forces in a fluid disposed between said collection area and said collection face to assist in removing a fluid disposed therebetween.

44. A system for separating a multi-component fluid for use in a device able to increase gravity, the system comprising:
a container including:
a bottom;
a side wall extending from said bottom generally along an axis, defining an interior of said container;
a first piston movable in said interior defining a cone having an apex within a volume defined by the first piston;
wherein said side wall is substantially rigid under ambient gravitational forces to substantially hold said first piston at a selected position in said interior;
wherein said side wall is able to compress axially along said axis and expand radially relative to said axis when under the increased gravitational forces such that said first piston is able to move axially in said interior.

45. The system of claim 44, wherein said sidewalls are formed of a material that is substantially inert to biological components.

46. The system of claim 44, wherein a pressure exerted externally on said sidewall further assists in holding said first piston in said selected position in said interior.

47. The system of claim 44, wherein an exterior dimension of said first piston is deformed to position said first piston into said container under ambient gravitational forces.

48. The system of claim 44, wherein an exterior dimension of said first piston is about 0.01 mm to about 1.50 mm smaller than a dimension of said interior under said increased gravitational forces.

49. A system to separate components of a multi-component fluid with a centrifuge, comprising:
a container defining a sample separation area;
a first piston selectively moveable between a first position and a second position in said sample holding area;
a piston rod able to move said first piston between said first position and said second position; and
a substantially automatic valve operably connected to said first piston;
a second piston independent of, but operable with said first piston to define a separation volume and including a surface operable to mate with the first piston;
wherein said substantially automatic valve allows a portion of the multi-component fluid to flow past said first piston as said first piston is moved within said sample separation area.

50. The system of claim 49, wherein said automatic valve includes a substantially one way valve that allows a material to flow in one direction but not in a second direction.

51. The system of claim 49, wherein said first piston moves through a component of said multi-component fluid to contain a selected volume of at least one of said components of the multi-component fluid or a substantial portion of a component of a multi-component fluid;
wherein such containment allows for removal of a selected portion of said multi-component fluid.

52. The system of claim 49, wherein a portion of the multi-component fluid flows past automatic valve as said first piston is able to selectively contain a selected volume of said multi-component fluid.

53. The system of claim 49, wherein said first piston is able to separate said sample separation area into a first sample collection area and a second sample collection area;
a port extending through said container to said first collection area.

54. The system of claim 53, further comprising:
a collapsible conduit extending from said port into said first collection area;
wherein said flexible conduit is able to substantially move with said first piston.

55. The system of claim 53, further comprising a filter system disposed in said container to allow for removal of a material from the first collection area.

56. The system of claim 49, further comprising:
a port extending from said container;
wherein said first piston is able to separate said sample separation area into a first sample collection area and a second sample collection area;
wherein said port allows for removal of a selected volume of the multi-component fluid after said first piston has formed said first collection area.

57. A kit for the separation and concentration of a selected component of a multi-component fluid with a centrifuge, comprising:
a first separation system and a second separation system, each separation system including:
a container substantially defining a sample containment area;
a first piston moveable within said container during a centrifugation of a sample positioned in said sample containment area;
a second piston movable within said sample containment area under an external manual force while the first piston remains substantially immobile;
a piston rod operably connected to said second piston to allow for said manual force to said second piston;
said second piston and said piston rods substantially defining a conduit;
said first piston and said second piston are able to substantially define a sample collection volume from which a volume of fluid may be withdrawn through said sample collection conduit;
a first syringe for operably connecting to said conduit to remove said volume of the multi-component fluid.

58. The kit of claim 57, further comprising a second syringe operable to do at least one of remove a biological component from an individual and position said biological component in said container.

59. The kit of claim 58, further comprising:
a third syringe able to operably connect to a port on said container to remove a second component of said multi-component fluid.

60. The kit of claim 57, wherein a sample may be removed from a patient and positioned in said container and a first component removed from the container in less than about 15 minutes.

* * * * *